United States Patent
Galey et al.

(10) Patent No.: US 9,067,900 B2
(45) Date of Patent: Jun. 30, 2015

(54) DIAMINOPHENOTHIAZINE COMPOUNDS, A METHOD FOR PREPARING SAME AND USES THEREOF

(75) Inventors: Laurent Galey, Emerainville (FR); Fabrice Peters, Paris (FR); Xavier Ferry, Strasbourg (FR)

(73) Assignee: PHARMA HYDRO DEVELOPMENT—P.H.D., Reims (FR)

( * ) Notice: Subject to any disclaimer, the term of this patent is extended or adjusted under 35 U.S.C. 154(b) by 0 days.

(21) Appl. No.: 12/677,030

(22) PCT Filed: Sep. 5, 2008

(86) PCT No.: PCT/FR2008/051588
§ 371 (c)(1),
(2), (4) Date: Mar. 8, 2010

(87) PCT Pub. No.: WO2009/044054
PCT Pub. Date: Apr. 9, 2009

(65) Prior Publication Data
US 2010/0204215 A1    Aug. 12, 2010

(30) Foreign Application Priority Data
Sep. 7, 2007 (FR) .................... 07 57406

(51) Int. Cl.
*C07D 279/20* (2006.01)
*A01N 43/84* (2006.01)
*C02F 1/50* (2006.01)

(52) U.S. Cl.
CPC ............. *C07D 279/20* (2013.01); *A01N 43/84* (2013.01); *C02F 1/50* (2013.01)

(58) Field of Classification Search
CPC .................................................. C07D 279/20
USPC ........................................................ 544/37
See application file for complete search history.

(56) References Cited

U.S. PATENT DOCUMENTS 5,220,009 A    6/1993    Mazur et al.

FOREIGN PATENT DOCUMENTS

| WO | 2005/034855 | 4/2005 |
|----|-------------|--------|
| WO | 2005/054217 | 6/2005 |
| WO | 2007/110627 | 10/2007 |

OTHER PUBLICATIONS

McCullough, J. Pathogen inactivation: a new paradigm for preventing transfusion-transmitted infections. 2007, American Society for Clinical Pathology, 128, 945-55.*
J. G. Michels et al., "Studies in the Sulfone Series", Journal of the American Chemical Society, vol. 72, Feb. 1920, pp. 888-892, XP002478603, US American Chemical Society, Washington, DC.
International Search Report dated Jul. 16, 2009, from corresponding PCT application.

* cited by examiner

*Primary Examiner* — Brian McDowell
(74) *Attorney, Agent, or Firm* — Young & Thompson

(57) ABSTRACT

Novel 2,8-diaminophenothiazine compounds of the following formula:

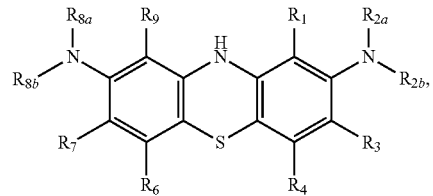

and a method for preparing the same, are presented. The 2,8-diaminophenothiazine compounds are useful in the field of treating liquid or gaseous fluids, especially influents and industrial or domestic effluents.

5 Claims, No Drawings

DIAMINOPHENOTHIAZINE COMPOUNDS, A METHOD FOR PREPARING SAME AND USES THEREOF

FIELD OF THE INVENTION

The present invention relates to novel diaminophenothiazine compounds and to a method for preparing the same.

The invention further relates to uses of novel diaminophenothiazine compounds in the field of treating liquid or gaseous fluids, especially industrial or domestic effluents.

PRIOR ART

Broadly speaking, there is a constant need in the state of the art for novel biocide agents for use in many various industrial fields where the use of such biocide agents and oxidizing agents is required, especially in the agro-food industry and in the effluent treatment field.

The microbiological risk represents a real threat because constantly evolving. Techniques and means implemented unavoidably select populations that are resistant to these techniques and means, or raise non-documented or old diseases. The actual systems relying on material sterilization and/or disinfection act as concentrators for living agents and molecules that resist to such treatments in question, thus jeopardizing human, animal and plant health (influents), and as tanks for the same products and risks (effluents).

Biocidal products and techniques intended to limit or to prevent any microbiological risk are outdated, both as regards general hygiene (disinfection, water potabilization, purification), and methods for treating the diseases and/or inconveniences that are associated with this population.

Fine and heavy industries such as pharmaceutical, agrifood, microelectronics industries, must produce under highly sterile and/or pure conditions.

Water and waste water treatment and purification are increasingly complex and expensive processes, in view of the worsening of the chemical or microbiological safety levels of the natural resources.

The more and more sophisticated invasive operations dedicated to the human and animal health require the influents (water, gas, atmospheres) to be rigorously disinfected. In 2007 the treatment of influents and effluents remains insufficiently controlled.

The number of nosocomial infections still remains excessively high.

The strong selection of traditional disinfectants (oxidizing agents, biguanides, quaternary ammonium compounds, etc.), makes it possible to limit usual human pathogenic microorganisms, but selects and hence introduces into the influent circuit microorganisms from various origins, for example biotelluric microorganisms (*Pseudomonas* spp. *Clostridrium* spp., *Cryptosporidium* spp., etc.). These novel agents appear to be very hard to treat and to eliminate.

As to antibiotics, their repeated use makes their action spectra towards traditional pathogenic bacteria collapse.

As already stated, disinfectants are frequently used in methods for treating industrial or domestic effluents. As an illustration, methods for treating effluents, should they be either of a domestic or an industrial origin, comprise generally the following successive steps:
- a lifting step for supplying the facility with the effluents to treat;
- a screening step intended to remove from the effluents to treat the coarsest solid pollutants through a physical separation process,
- a so called "primary treatment" step consisting in a physical separation step for removing most part of the suspended materials, such step typically consisting in a physical separation step through settling. Such settling separation step is commonly performed after having previously caused the pollutants to flocculate. The pollutant flocculation is produced by adding flocculating agents to the decanting vessel, such as metal salts for example, thus making the suspended materials and some other organic and inorganic pollutants precipitate (flocculate).
- a so called "secondary treatment" step intended to remove carbonaceous or nitrogenous pollutants, which typically use bacteria-mediated biological processes, said bacteria being optionally immobilized onto supports, including filter membranes;
- a disinfection step intended to eliminate unwanted unicellular or multi-cellular organisms including unwanted microorganisms, which may be carried out by adding to the treated effluents a biocide agent, before they are released into the natural environment. Said disinfection step is commonly carried out by adding chlorine. Such disinfection step mediated through oxidizing agents may also be carried out by adding biocide agents such as ozone or bromine, and under some circumstances chlorine dioxide. Alternatively, the disinfection step may be carried out by submitting effluents to solar radiation or to an artificial ultraviolet radiation, in order to kill the unwanted living organisms;
- an effluent clarification step, which typically consists in a final settling step so as to separate the purified effluent and the secondary sludge or residues resulting from organic material degradation, prior to releasing the purified and disinfected effluent into the natural environment.

Effluents of human or animal origin comprise an average microbial load of from $10^5$ to $10^7$ bacteria/ml which may be regenerated at 22° C. In water-treatment plants, microorganisms originating from human and animal gastrointestinal tracts may interfere with the water normal bacterial population. It results therefrom an exchange and a transfer of the genetic material, amongst which antibiotic resistance genes. Bacteria crossing the chlorine-ozone barrier, that are normally present in reservoirs and sources drinking water, thus become resistant to antibiotics. The reverse process may also occur: ingesting drinking water (either treated or originating from a source) may induce the same transfer to the normal intestinal bacteria. The vicious circle is complete.

A method is known for producing in situ highly reactive products through organic synthesis. It proceeds through photochemical action and is able to generate reactive states within organic molecules and especially singlet oxygen starting from triplet oxygen, under the action of a photon. The molecules that are able to induce such a reaction are said to be photosensibilizers; the photon energy excites the photosensibilizer, which in turn transfers this energy to a further molecule. If this molecule is oxygen, the molecule from the less reactive triplet state goes to the highly reactive singlet state (type II reaction, C. S. Foote, Photochem. Photobiol., 1991: 54,659). Such singlet oxygen is a non-radical form which may generate superoxide anion radicals, that are themselves highly reactive.

Organic chemistry uses various photosensibilizers to produce radicals from neutral molecules, carbonyl derivatives (acetone, benzophenone, menadione) and dyes (rose bengal, methylene blue).

The methylene blue series (diamino 3,7-phenothiazine, see supra) is particularly interesting. This molecule (and derivatives thereof) is a common histological dye, less toxic, provided with many biological and pharmacological properties which has a moderate antiseptic action (bacteriostat) and is an antidote to nitrites and methemoglobinizing poisonings. Its photoactivable properties (biocidal singlet oxygen generating product) are already employed as sterilizing agents for blood-derived products. Starting from the 3,7-diaminophenothiazine structure exclusively, a great number of derivatives have been synthesized. Various authors have demonstrated the interest of such products upon photoactivation, in the treatment of skin diseases, as a general biocide for prokaryotes and eukaryotes, etc. (See for example state of the art in WO 2005/054217 A1, WO 2005/034855 A2).

However, derivatives from the family of 3,7-diaminophenothiazine consist in ionic structures, in the form of unstable ammonium compounds. These compounds provide few specific improvements to the methylene blue. In addition, the photoactivation of these compounds can only be accomplished with an ultraviolet radiation.

The applicant strove to synthesize novel biocide agents for use generally as disinfectants, including disinfectants in methods for treating polluted effluents.

SUMMARY OF THE INVENTION

The present invention relates to novel 2,8-diaminophenothiazine biocidal compounds of formula (I) defined hereafter in the present description.

It is also an object of the present invention to provide a method for preparing 2,8-diaminophenothiazine compounds of formula (I).

The invention further relates to the use of the novel 2,8-diaminophenothiazine compounds of formula (I) as biocide agents.

DETAILED DESCRIPTION OF THE INVENTION

The present invention provides novel biocidal compounds derived from the family of the 2,8-diaminophenothiazines.

For all the applicant knows, the only known compounds derived from the family of the 2,8-diaminophenothiazines are respectively the diamine unsubstituted compound and the acylated precursor thereof. These products have been prepared by performing a first diacetylation step of the phenothiazine, followed with a second step of generating the oxime and making the rearrangement thereof according to the Beckman reaction, as described by Chien and al. (J. Med. Chem., 1966, Vol. 9: 960-962). A method has also been described comprising a first step of converting the diketone to diacid, followed with a second step of activating these functions in the form of acid chloride, thereafter a step of transforming the resulting product to acylazide prior to performing a transposition step to obtain the diamine (Michels and al., 1950, J. Am. Chem. Soc., Vol. 72: 888-892). Michels and al. (1950) also describe a method comprising a step of converting 2-bromomo-4-nitroaniline bromide to the corresponding thiophenol compound. Thereafter the thiophenol compound is fused to the 3,4-diiodonitrobenzene, prior to an Ullmann intramolecular coupling reaction to obtain the 2,8-dinitrophenothiazine which is then reduced to 2,8-diaminophenothiazine. Chien and al. (1966, Supra) do not suggest to test any biological activity of the 2,8-diaminophenothiazine compound, which is just an intermediate compound for obtaining the 2,8-diaminophenothiazine-5,5-dioxide end product.

Surprisingly, it has been demonstrated according to the invention that these novel 2,8-diaminophenothiazine compounds possess, after photoactivation, a biocidal activity towards a great variety of microorganisms and, as a consequence, that these novel compounds are useful as biocides, and especially as disinfectants. The DAP-2,8 tetramethyl compound(s) (or others) present(s) surprisingly a flocculating activity for proteins and/or bacterial culture media components, of the yeast extract or animal albumin type, never described neither about the DAP 3-7 series nor about the earlier 2-8 dioxamines.

In protein-enriched medium (bovine albumin (BSA) or yeast extract), DAP-2,8 tetramethyl spontaneously flocculates the media and concentrates within the pellet. The solution from the initial yellow turns to an intense blue-green shade. There is a dose-to-effect relationship with from 0.3 to 10 g/l of protein, with the precipitation of the proteins-bacteria-DAP mixture. This unexpected property enables a global approach of the wastewater treatment, enabling one single step of flocculation/settling/disinfection. These products, especially in the form of water-soluble dichlorhydrates, have a bactericidal activity towards different strains of gram +(*Staphylococcus aureus*), and gram–(*E. coli, Pseudomonas aeruginosa Legionella peumophila*) bacteria. The product also possess an activity towards filamentous eukaryotes, for example *Candida albicans*. This DAP 2-8 spectrum (bactericidal against gram –) is totally different from that of the 3-7 diaminophenothiazines (bacteriostat strictly directed against gram +).

According to standardized methods, the infectious titer reduction may attain up to 8 log at 30 mm under a white light, i.e. 10000 times more than methylene blue control under the same conditions. This activity is effective from the 0.05 g/l concentration, i.e. 0.05 per thousand (weight/weight). The effect also exists in the dark but it occurs later (by a factor of 2 at least).

In addition, the applicant did develop an original method for preparing these novel 2,8-diaminophenothiazine biocidal compounds.

It is an object of the invention to provide a 2,8-diaminophenothiazine compound (DAP-2,8) of following formula (I):

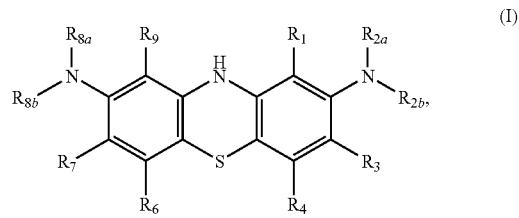

wherein:

(i) $R_1$, $R_3$, $R_4$, $R_6$, $R_7$ and $R_9$ groups each represent, independently from one another a group selected from:
  a hydrogen atom,
  a halogen,
  an alkyl group having from 1 to 12 unsubstituted carbon atoms,
  an alkyl group having from 1 to 12 carbon atoms substituted by a phenyl group, said phenyl group being:
    either unsubstituted,
    or substituted by one or more groups selected from a halogen, a hydroxy, an alkyl having from 1 to 12 carbon atoms, and an alkoxy having from 1 to 12 carbon atoms, (ii) $R_{2a}$, $R_{2b}$, $R_{8a}$ and $R_{8b}$ groups each represent, independently from one another a group selected from:
- a hydrogen atom,
- an alkyl group, a hydroxyalkyl group or an alkoxyalkyl group having from 1 to 12 unsubstituted carbon atoms,
- an alkyl group or an alkoxyalkyl group having from 1 to 12 carbon atoms substituted by a phenyl group, said phenyl group being:
- either unsubstituted,
- or substituted by a group selected from
   - a halogen,
   - a hydroxy,
   - an alkyl having from 1 to 12 carbon atoms,
   - an alkoxyalkyl having from 1 to 12 carbon atoms,
   - an alkenyl having from 2 to 12 carbon atoms, unsubstituted or substituted by a group selected from a halogen, a hydroxy, an alkyl having from 1 to 12 carbon atoms, an alkoxy having from 1 to 12 carbon atoms,
   - an alkynyle having from 2 to 12 carbon atoms, unsubstituted or substituted by a group selected from a halogen, a hydroxy, an alkyl having from 1 to 12 carbon atoms, an alkoxy having from 1 to 12 carbon atoms,
   - a cycloalkyl having from 4 to 12 carbon atoms, unsubstituted or substituted by a group selected from a halogen, a hydroxy, an alkyl having from 1 to 12 carbon atoms, an alkoxy having from 1 to 12 carbon atoms,
   - a cycloalkenyl having from 4 to 12 carbon atoms, unsubstituted or substituted by a group selected from a halogen, a hydroxy, an alkyl having from 1 to 12 carbon atoms, an alkoxy having from 1 to 12 carbon atoms, (iii) or —$NR_{2a}R_{2b}$ or —$NR_{8a}R_{8b}$ groups, independently from one another, represent a heterocycle having from 4 to 12 carbon atoms, either saturated or unsaturated, where said heterocycle may comprise one or more additional heteroatoms selected from nitrogen, oxygen and sulfur, said heterocycle being unsubstituted or being substituted by a group selected from a halogen, a hydroxy and an alkyl having from 1 to 12 carbon atoms, as well as any optical isomer, stereoisomer, diastereoisomer, enantiomer or racemic mixture of a compound of formula (I),
as well as salts, hydrates, solvates and polymorphic forms of a compound of formula (I), except compounds of formula (I), wherein each of the groups selected from $R_1$, $R_{2a}$, $R_{2b}$, $R_3$, $R_4$, $R_5$, $R_7$, $R_{8a}$, $R_{8b}$ and $R_9$ represents a hydrogen atom.

In the present invention, said halogen is selected from chlorine, fluorine, bromine and iodine atoms.

As used herein, an "alkyl" is intended to mean a linear or a branched chain of a monovalent, saturated hydrocarbon radical and having the specified number of carbon atoms. In a branched alkyl group, the linear hydrocarbon chain is substituted by one or more alkyl groups. Alkyl groups include methyl, ethyl, propyl, butyl, pentyl and hexyl groups.

As used herein, an "alkoxy" is intended to mean a linear or a branched chain of a saturated, monovalent hydrocarbon alcohol radical resulting from the removal of a hydrogen atom in a hydroxy group. Typically, an alkoxy group has the general formula "R—O—", R being an alkyl group.

As used herein, an "alkoxyalkyl" is intended to mean an alkyl chain interrupted by an oxygen atom and which has the specified number of carbon atoms. Typically, an alkoxyalkyl group has the general formula "R—O—R'—", wherein R and R' each represent to an alkyl group.

As used herein, an "alkenyl" is intended to mean a linear or a branched chain of a monovalent, partially unsaturated hydrocarbon radical having at least one carbon-carbon double bond and possessing the specified number of carbon atoms. The conformation of the atoms bound to the double bond carbon atoms may be equally cis-(Z) or trans-oriented. Alkenyl groups include ethenyl, propenyl and butenyl groups. In a branched alkenyl group, the unsaturated linear hydrocarbon chain is substituted by one or more alkyl or alkenyl groups. Alkyl substituents include methyl, ethyl or propyl groups. Alkenyl substituents include vinyl, allyl, and prop-1-enyl groups.

As used herein, an "alkynyl" is intended to mean a linear or a branched chain of a monovalent radical, having at least one carbon-carbon triple bond and possessing the specified number of carbon atoms. Alkynyl groups include ethynyl, propynyl and butynyl groups. In a branched alkynyl group, the unsaturated linear chain is substituted by one or more alkyl, alkenyl or alkynyl groups. Alkyl substituents include methyl, ethyl or propyl groups. Alkenyl substituents include vinyl, allyl, and prop-1-enyl groups. Alkynyl substituents include ethynyl, propargyl and prop-1-yn-1-yl groups.

As used herein, a "cycloalkyl" is intended to mean a monocyclic or polycyclic saturated, hydrocarbon radical. Cycloalkyl groups include cyclobutyl, cyclopentyl, cyclohexyl, cycloheptyl and cyclooctyl monocyclic groups. Cycloalkyl groups also include norbornane and decaline polycyclic groups.

As used herein, a "cycloalkenyl" is intended to mean a monocyclic or polycyclic, partially unsaturated, hydrocarbon radical, having at least one carbon-carbon double bond. Cycloalkenyl groups include cyclobutenyl, cyclopentenyl, cyclopentadienyl, cyclohexenyl, cycloheptenyl and cyclooctenyl monocyclic groups. Cycloalkenyl groups also include adamantane and norbornene polycyclic groups.

As used herein, a "heterocycle" is intended to mean a saturated or partially unsaturated, monocyclic hydrocarbon system, wherein at least one carbon atom is replaced with a heteroatom selected from nitrogen, oxygen and sulfur. Heterocyclic groups include pyrrolidine, piperidine, morpholine, thiomorpholine, 1,4-dioxa-8-azaspiro[4,5]decane and 1,2,3,6-tetrahydropyridine groups. Heterocyclic groups also include groups of this type described in "Handbook of Chemistry and Physics, $76^{th}$ edition, CRC Press, Inc., 1995-1996", pages 2-25 to 2-26, this extract being incorporated therein as a reference.

As used herein, "substituted" is intended to mean a reference group wherein at least one of the hydrogen atoms is replaced with a separate chemical group.

Generally, whatever the substituent in question, an alkyl group having from 1 to 12 carbon atoms preferably consists in an alkyl group having from 1 to 6 carbon atoms.

For $R_1$, $R_3$, $R_4$, $R_6$, $R_7$ and $R_9$ groups, the alkyl group, substituted or not, preferably consists in an alkyl group having from 1 to 6 carbon atoms.

For $R_1$, $R_3$, $R_4$, $R_6$, $R_7$ and $R_9$ groups substituted by a phenyl group, the phenyl group being substituted by one or more alkyl or alkoxy groups, the alkyl group or the group alkoxy having from 1 to 12 carbon atoms preferably consists in an alkyl or alkoxy group having from 1 to 6 carbon atoms.

For $R_{2a}$, $R_{2b}$, $R_{8a}$ and $R_{8b}$ groups, the unsubstituted or substituted alkyl, hydroxyalkyl or alkoxyalkyl group preferably consists in an alkyl, hydroxyalkyl or alkoxyalkyl group having from 1 to 6 carbon atoms.

For $R_{2a}$, $R_{2b}$, $R_{8a}$ and $R_{8b}$ groups substituted by a phenyl group, the phenyl group being itself substituted by an alkyl group, said alkyl group has preferably from 1 to 6 carbon atoms.

For $R_{2a}$, $R_{2b}$, $R_{8a}$ and $R_{8b}$ groups substituted by a phenyl group, the phenyl group being itself substituted by an alkoxyalkyl group, said alkoxyalkyl group has preferably from 1 to 6 carbon atoms.

For $R_{2a}$, $R_{2b}$, $R_{8a}$ and $R_{8b}$ groups substituted by a phenyl group, the phenyl group being itself substituted by an alkenyl group, said alkenyl group has preferably from 2 to 6 carbon atoms.

For $R_{2a}$, $R_{2b}$, $R_{8a}$ and $R_{8b}$ groups substituted by a phenyl group, the phenyl group being itself substituted by an alkynyl group, said alkynyl group has preferably from 2 to 6 carbon atoms.

For $R_{2a}$, $R_{2b}$, $R_{8a}$ and $R_{8b}$ groups substituted by a phenyl group, the phenyl group being itself substituted by a cycloalkyl group, said cycloalkyl group has preferably from 4 to 6 carbon atoms.

For $R_{2a}$, $R_{2b}$, $R_{8a}$ and $R_{8b}$ groups substituted by a phenyl group, the phenyl group being itself substituted by a group cycloalkenyl, said group cycloalkenyl has preferably from 4 to 6 carbon atoms.

The various isomers of compounds of formula (I), including optical isomers, enantiomers, stereoisomers and diastereoisomers are defined through the presence of one or more asymmetric centers in the structure of such compounds, based on the determination of absolute stereochemistry, like the different (R-) or (S-) forms of said asymmetric centers. The various isomers of compounds of formula (I), including optical isomers, enantiomers, stereoisomers and diastereoisomers are prepared according to methods well known from the one skilled in the art (see "Molécules chirales Stéréochimie et propriétés" André COLLET, Jean CRASSOUS, Jean-Pierre DUTASTOU, Laure GUY—Jan. 1, 2006—EDP SCIENCES Isbn: 2-86883-849-9).

The invention includes salts of compounds of formula (I), including addition salts with inorganic acids such as chlorhydrates, bromhydrates, sulfates, nitrates and phosphates. The invention also includes addition salts with organic acids such as acetates, propionates, succinates, maleates, fumarates, methanesulfonates, p-toluenesulfonates, and isethionates. Preferred salts of compounds of formula (I) consist in salts described by P. H. Stahl and C. G. Wermuth in "Handbook of Pharmaceutical salts, Properties, Selection and Use, Wiley-VCH, 2002" and in "Remington's Pharmaceutical Sciences, 17$^{th}$ edition, Mack Publishing Company, Easton, Pa., 1985", page 1418.

The invention also includes hydrates of compounds of formula (I) which may be obtained for example:
(a) by drying wet crystals of compounds of formula (I) at a low temperature, for example at a temperature ranging from 20° C. to 50° C., preferably from 20° C. to 40° C., and for a time period ranging from 6 hours to 72 hours, preferably from 12 hours to 24 hours, or
(b) by drying crystals of compounds of formula (I) at a high temperature, for example at a temperature ranging from 80° C. to 130° C., preferably from 90° C. to 120° C., then by submitting the dried crystals to a wet atmosphere, for example an atmosphere with a moisture content ranging from 40% to 100% saturation, and for a time period ranging from 6 hours to 72 hours, preferably from 12 hours to 24 hours.

Forming a hydrate of a compound of formula (I) may be confirmed by measuring the water content of the resulting hydrate which should correspond to that water content expected for said hydrate, for example by using the Karl Fischer method and by submitting said hydrate to a differential scanning calorimetry measurement, as is well known from the person skilled in the art.

Surprisingly, compounds of formula (I) are present in two forms, respectively as bases and as solvates, including when they are in the form of salts, for example salts with halogens, or with saturated or unsaturated acids, including alkyl carboxylic acids.

Solvates of compounds of formula (I) may be prepared according to traditional methods with which the person skilled in the art is familiar, for example by dissolving a compound of formula (I) in solvents such as water, methanol or ethanol, thereafter by recrystallizing said compound by means of an also traditional crystallization technique.

Generally, compounds of formula (I) may be solvated in a hydrophobic medium. These compounds may for example be immobilized onto supports, inert or not, for example onto the surface of membrane filters, including those membrane filters commonly used for implementing methods for treating industrial or domestic effluents.

Compounds of formula (I) may also be solvated in a hydrophilic medium, for example by being directly added to the fluid to be treated, such as waste waters and waste fluids, or influents or effluents of various origins. Compounds of formula (I) may especially be added to treatment facilities in closed or opened systems, for example in air conditioning, dialysis or gas circuits, in systems for odor removal, COV or micropollutant control and to eliminate any other product sensitive to oxidation and that may be removed through such method.

Polymorphic forms of compounds of formula (I) include the various crystalline forms of these compounds.

In some embodiments of compounds of formula (I), $R_{2a}$ groups and $R_{2b}$ groups each represent a hydrogen atom.

In some embodiments of compounds of formula (I), $R_{8a}$ groups and $R_{8b}$ groups each represent a hydrogen atom.

In some embodiments of compounds of formula (I) wherein $R_{2a}$, $R_{2b}$, $R_{8a}$ and $R_{8b}$ groups each represent, independently from one another an alkyl group, a hydroxyalkyl group or an alkoxyalkyl group having from 1 to 12 carbon atoms substituted by a phenyl group, said phenyl group being substituted by a group selected from
a halogen,
an alkenyl, alkynyl, cycloalkyl or cycloalkenyl group, said group being substituted by a halogen,
said halogen being preferably a fluorine.

In some embodiments of compounds of formula (I) wherein —$NR_{2a}R_{2b}$ or —$NR_{8a}R_{8b}$ groups, independently from one another, represent a heterocycle having from 4 to 12 carbon atoms, either saturated or unsaturated, where said heterocycle may comprise one or more additional heteroatoms selected from nitrogen, oxygen and sulfur, said heterocycle being unsubstituted or being substituted by a group selected from a halogen, said halogen being preferably a fluorine.

Compounds of formula (I) according to the invention include following compounds:
N,N,N',N'-Tetramethyl-10H-phenothiazine-2,8-diamine
N,N-Dimethyl-[8-(4-methylpiperazin-1-yl)-10H-phenothiazin-2-yl]amine
N,N-Dimethyl-(8-morpholin-4-yl-10H-phenothiazin-2-yl)amine
N,N-Diethyl-N',N'-dimethyl-10H-phenothiazine-2,8-diamine
N,N-Diethyl-[8-(4-methyl-piperazin-1-yl)-10H-phenothiazin-2-yl]amine N,N-Diethyl-(8-morpholin-4-yl-10H-phenothiazin-2-yl)amine
N,N-Dimethyl-N',N'-dipropyl-10H-phenothiazine-2,8-diamine
[8-(4-Methyl-piperazin-1-yl)-10H-phenothiazin-2-yl]-dipropylamine
(8-Morpholin-4-yl-10H-phenothiazin-2-yl)-dipropylamine
N,N-Dibutyl-N',N'-dimethyl-10H-phenothiazine-2,8-diamine
N,N-Dibutyl-[8-(4-methylpiperazin-1-yl)-10H-phenothiazin-2-yl]amine
N,N-Dibutyl-(8-morpholin-4-yl-1 OH-phenothiazin-2-yl)amine
N,N-Dimethyl-N'-propyl-10H-phenothiazine-2,8-diamine
3,N,N,N',N'-Pentamethyl-10H-phenothiazine-2,8-diamine
2-[N-(8-Dimethylamino-10H-phenothiazin-2-yl)-N-(2-hydroxyethyl)amino]ethanol Method for Preparing Compounds of Formula (I)

The applicant did develop a method for specifically preparing compounds of formula (I), which is easy and fast to implement, and which in particular makes it possible to readily introduce various types of substituents, either onto amine functions ($R_{2a}$, $R_{2b}$, $R_{8a}$ and $R_{8b}$ groups) or onto aromatic rings ($R_1$, $R_3$, $R_4$, $R_6$, $R_7$ and $R_9$ groups) of the 2,8-diaminophenothiazines of the invention.

General Method (Step b)

It is also an object of the invention to provide a method for preparing a 2,8-diaminophenothiazine compound of following formula (I'):

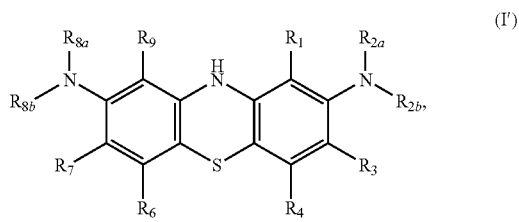

wherein:
(i) $R_1$, $R_3$, $R_4$, $R_6$, $R_7$ and $R_9$ groups each represent, independently from one another a group selected from:
a hydrogen atom,
a halogen,
an alkyl group having from 1 to 12 unsubstituted carbon atoms,
an alkyl group having from 1 to 12 carbon atoms substituted by a phenyl group, said phenyl group being:
either unsubstituted,
or substituted by one or more groups selected from a halogen, a hydroxy, an alkyl having from 1 to 12 carbon atoms, and an alkoxy having from 1 to 12 carbon atoms,
(ii) $R_{2a}$, $R_{2b}$, $R_{8a}$ and $R_{8b}$ groups each represent, independently from one another a group selected from:
a hydrogen atom,
an alkyl group or an alkoxyalkyl group having from 1 to 12 unsubstituted carbon atoms,
an alkyl group, a hydroxyalkyl group, or an alkoxyalkyl group having from 1 to 12 carbon atoms substituted by a phenyl group, said phenyl group being:
either unsubstituted,
or substituted by a group selected from
a halogen,
a hydroxy,
an alkyl having from 1 to 12 carbon atoms,
an alkoxy having from 1 to 12 carbon atoms,
an alkenyl having from 2 to 12 carbon atoms, unsubstituted or substituted by a group selected from a halogen, a hydroxy, an alkyl having from 1 to 12 carbon atoms, an alkoxy having from 1 to 12 carbon atoms,
an alkynyle having from 2 to 12 carbon atoms, unsubstituted or substituted by a group selected from a halogen, a hydroxy, an alkyl having from 1 to 12 carbon atoms, an alkoxy having from 1 to 12 carbon atoms,
a cycloalkyl having from 4 to 12 carbon atoms, unsubstituted or substituted by a group selected from a halogen, a hydroxy, an alkyl having from 1 to 12 carbon atoms, an alkoxy having from 1 to 12 carbon atoms,
a cycloalkenyl having from 4 to 12 carbon atoms, unsubstituted or substituted by a group selected from a halogen, a hydroxy, an alkyl having from 1 to 12 carbon atoms, an alkoxy having from 1 to 12 carbon atoms,
(iii) or —$NR_{2a}R_{2b}$ or —$NR_{8a}R_{8b}$ groups, independently from one another, represent a heterocycle having from 4 to 12 carbon atoms, either saturated or unsaturated, where said heterocycle may comprise one or more additional heteroatoms selected from nitrogen, oxygen and sulfur, said heterocycle being unsubstituted or being substituted by a group selected from a halogen, a hydroxy and an alkyl having from 1 to 12 carbon atoms,
said method comprising a step (b) during which the diphenylamine compound of following formula (II):

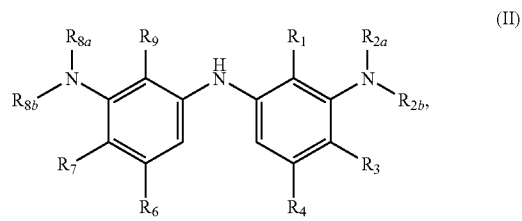

wherein $R_1$, $R_{2a}$, $R_{2b}$, $R_3$, $R_4$, $R_5$, $R_7$, $R_{8a}$, $R_{8b}$ and $R_9$ groups have the same meaning as for compound of formula (I),
is submitted to a heating step selected from:
(b1) a heating step at a temperature ranging from 60° C. to the boiling temperature of the reaction mixture in the presence of iodine and sulfur in an inert solvent such as an aromatic solvent, an alkane or a polyhalogenoalkane for a time period ranging from 1 hour to a night;
(b2) a microwave heating step for a time period ranging from 10 seconds to six times ten minutes;
(b2-1) either of a combination of the compound of formula (II) with iodine and sulfur, with no solvent or in the presence of an inert solvent such as an aromatic solvent, an alkane or a polyhalogenoalkane;
(b2-2) or of a combination of the compound of formula (II) with iodine and sulfur, the compound of formula (II), iodine and sulfur being adsorbed onto a support such as silica, alumina or a zeolite, so as to obtain the compound of formula (I).

To perform step b1), a mixture is preferably used as starting material comprising the compound of formula (I), sulfur and iodine in a heating step under reflux, in a solvent, which boiling point is adapted to the chosen reaction temperature.

Preferably, in step b1), the heating temperature ranges from 100° C. to the boiling temperature of the reaction mixture.

In step b1) a solvent may be especially used, selected from toluene, xylene (ortho-xylene, meta-xylene, para-xylene), durene, isodurene, (ortho-, meta- or para-) dichloro-benzene, ethyl benzene, pentamethyl benzene, hexamethyl benzene, mesitylene, cumene or hemimellitene. Orthodichlorobenzene is preferably used.

In step b1), the compound of formula (I) and sulfur are used in a compound (I)-to-sulfur molar ratio ranging from 0.2:1 to 1:1, for example a molar ratio ranging from 0.3:1 to 0.5:1, such as of about 0.4:1.

In step b1), iodine may be added in the form of an iodine crystal.

Step b1) is preferably carried out under an inert, and where possible anhydrous, atmosphere, for example under argon, nitrogen or dinitrogen atmosphere.

In some embodiments, duration of step b1) may last from 2 hours to 4 hours. It may last about 3 hours.

After heating, the temperature of the reaction mixture is decreased to room temperature, then the corresponding compound of formula (I) is recovered.

In some embodiments, the compound of formula (I) is recovered and extracted by adding a suitable solvent selected from traditional suitable solvents, which are well known from the person skilled in the art. As an illustration, the resulting compound of formula (I) may be extracted with diethyl ether, then optionally filtered and concentrated under reduced pressure.

When appropriate, the oily fluid containing the compound of formula (I) is submitted to a purification final step. Such purification step may consist in a chromatography step, for example on a silica gel, prior to eluting the compound of formula (I), when appropriate with toluene, in order to provide a powdered compound of formula (I).

To perform an alternative step b2), heating is performed by submitting the compound of formula (II) and the one or more reactants associated therewith to a microwave radiation.

In a first embodiment of alternative step b2), hereabove referred to as b2-1), heating is performed by submitting to a microwave radiation a mixture comprising the compound of formula (II), iodine and sulfur, in order to obtain, then to recover, the corresponding compound of formula (I). The conditions of the reaction are substantially the same as those described for step b1) hereabove, except the parameters that are specific to heating strictly speaking.

A microwave radiation is typically used with a power ranging from 150 to 500 Watts, the power range extending suitably from 70 to 700 W. In a second embodiment of alternative step b2), hereabove referred to as b2-1), heating is performed by submitting to the microwave radiation a mixture comprising a compound of formula (II) with iodine and sulfur, iodine and sulfur being adsorbed onto a support. The conditions of the reaction are substantially the same as those described for step b1) hereabove, except the parameters that are specific to heating strictly speaking, which are similar or the same as the heating parameters described for the first embodiment hereabove referred to as b2-1).

Suitable support types for immobilizing sulfur and iodine include for example alumina, silica or a zeolite.

Step a) of the Method

As a rule, the various compounds of formula (II) used as raw materials for implementing the method for preparing compounds of formula (I) may be obtained through any method known from the person skilled in the art.

However, the applicant did develop methods for preparing compounds of formula (II), said methods consisting in specific embodiments of the general method for preparing compounds of formula (I) previously described.

Step a) First Alternative of the Method

Thus, in a first specific embodiment, the method for preparing a compound of formula (I) such as defined hereabove is characterized in that it comprises a step (a) for obtaining a compound of formula (II), which is performed prior to step b), wherein a compound of following formula (III):

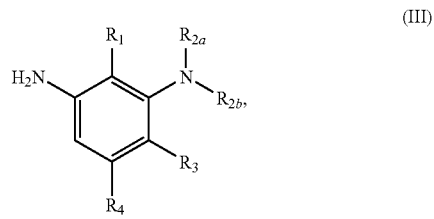

wherein $R_1$, $R_{2a}$, $R_{2b}$, $R_3$ and $R_4$ groups have the same meaning as in claim 1, is reacted with a compound of following formula (IV):

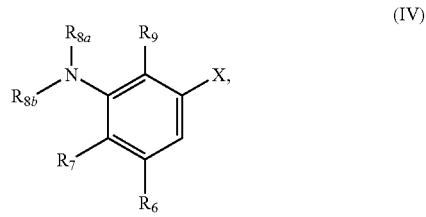

wherein $R_5$, $R_7$, $R_{8a}$, $R_{8b}$ and $R_9$ groups have the same meaning as in claim 1 and X represents a halogen or a sulfonate group,
in the presence of a palladium or a nickel catalyst and a catalyst ligand, together with an organic or inorganic base,
at a temperature ranging from 80° C. to 110° C. and for a time period ranging from 8 to 15 hours
for obtaining the compound of formula (II).

In some embodiments, X represents a halogen selected from bromine, chlorine and iodine.

In other embodiments, X represents a sulfonate selected from a triflate, a mesylate, a tosylate, a nosylate and a nonaflate.

In some embodiments, the catalyst consists in a platinum-based catalyst, for example a Pd(dba)$_2$ catalyst.

In some embodiments, the catalyst ligand is selected from dppa (bis(diphenylphosphino)amine), dppf (1,1'-bis(diphenylphosphino)ferrocene), BINAP, josiphospyphos (6-diphenylphosphino-2-pyridonate), QUINAP, Pyphos and Qphos, which are catalyst ligands well known from the one skilled in the art. Dppf will be advantageously used.

In some embodiments, the organic base consists in an alkali carbonate or in sodium tert-butylate.

The reactant mixture is advantageously dissolved in a suitable solvent, which may be selected from toluene, xylene (ortho-xylene, meta-xylene, para-xylene), durene, isodurene, (ortho-, meta- or para-) dichloro-benzene, ethyl benzene, pentamethyl benzene, hexamethyl benzene, mesitylene-cumene and hemimellitene. Preferably, ortho dichloro-benzene will be used.

Advantageously, the compound (III):(IV) molar ratio in the reaction mixture ranges from 0.5:1 to 1:0.5, preferably from 0.8:1 to 1.2:1, and is most preferably of about 1.

After heating, the temperature of the reaction mixture is decreased to room temperature, then the corresponding compound of formula (II) is recovered.

In some embodiments, the compound of formula (II) is recovered and extracted by adding a suitable solvent selected from traditional suitable solvents, which are well known from the one skilled in the art. The resulting compound of formula (II), after extraction, may be filtered and concentrated under reduced pressure.

In other embodiments, the resulting compound of formula (II) is purified by flash chromatography, for example by using a suitable solvent gradient. As an illustration, a gradient from 5% (v/v) to 12% (v/v) of ethyl acetate in hexane may be used, as illustrated in the examples.

Step a) Second Alternative of the Method

In a second specific embodiment, the method for preparing a compound of formula (I) such as defined hereabove is characterized in that it comprises a step (a) for obtaining a compound of formula (II), which is performed prior to step b), wherein a compound of following formula (III):

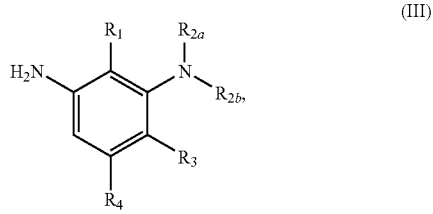

wherein $R_1$, $R_{2a}$, $R_{2b}$, $R_3$ and $R_4$ groups have the same meaning as in claim 1, is reacted with a compound of following formula (IV):

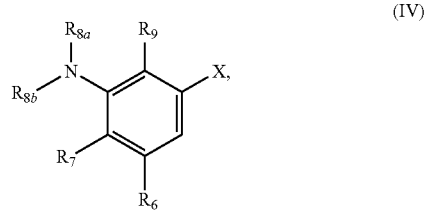

wherein $R_5$, $R_7$, $R_{8a}$, $R_{8b}$ and $R_9$ groups have the same meaning as in claim 1 and X represents a halogen or a sulfonate group, in the presence of a salt or copper oxide together with an organic base at a temperature ranging from 40° C. to the boiling temperature of the reaction mixture for a time period ranging from 2 hours to a night for obtaining the compound of formula (II).

In some embodiments, X represents a halogen selected from bromine, chlorine and iodine.

In other embodiments, X represents a sulfonate selected from a triflate, a mesylate, a tosylate, a nosylate and a nonaflate.

In some embodiments, the organic base consists in an alkali carbonate such as sodium carbonate, potassium carbonate and cesium carbonate.

In some embodiments, the copper salt is selected from copper halides.

Other Alternatives for Preparing Compounds of Formula (I)

Compounds of formula (I) may also be prepared starting from compounds of formula (I) wherein $R_{2a}$, $R_{2b}$, $R_{8a}$ or $R_{8b}$ represent a hydrogen atom, by alkylation, reductive amination or by acylation followed with a reduction.

When proceeding through an alkylation, the amine is fused to an alkyl halide or a sulfonate in the presence of an inorganic base such as a metal carbonate or bicarbonate or an organic base such as a tertiary amine.

When proceeding through a reductive amination, the amine is fused to a ketone or an aldehyde in the presence of a reducing agent such as dihydrogen or a dihydrogen donor (formate, cyclohexene for example) in the presence or in the absence of a transition metal such as palladium. It is also possible to use as a reducing agent a hydride such as sodium cyanoborohydride, sodium triacetoxyborohydride or sodium borohydride.

When proceeding through an acylation followed with a reduction, acylation may be carried out by the action of a symmetric or mixed anhydride, an acid chloride or an acid in the presence of a coupling agent such as a carbodiimide, carbonyl diimidazole or another peptide coupling agent, optionally in the presence of a catalyst such as 4-dimethyl aminopyridine, hydroxybenzotriazole (HOBT) or HOAT and of an organic or inorganic base. Reduction may then be carried out using lithium aluminium double hydride.

So, according to a further embodiment of the method for preparing a compound of formula (I) of the invention, said method is characterized in that a compound of formula (I') wherein at least one of the groups selected from $R_1$, $R_{2a}$, $R_{2b}$, $R_3$, $R_4$, $R_5$, $R_7$, $R_{8a}$, $R_{8b}$ and $R_9$ is not a hydrogen atom and is prepared from a compound of formula (I") wherein each of the groups selected from $R_1$, $R_{2a}$, $R_{2b}$, $R_3$, $R_4$, $R_5$, $R_7$, $R_{8a}$, $R_{8b}$ and $R_9$ represents a hydrogen atom according to the following steps:

c) a reaction step selected from an alkylation step, a reductive amination step or an acylation step; and d) a reduction step.

Compounds of formula (I) wherein $R_1$, $R_3$, $R_4$, $R_6$, $R_7$ or $R_9$ is different from hydrogen may be prepared starting from compounds of formula (I) wherein $R_1$, $R_3$, $R_4$, $R_6$, $R_7$ or $R_9$ represents a hydrogen atom, through aromatic ring functionalization methods, which are known from the one skilled in the art, including but without limitation halogenations, directed metallations, Friedel reactions and rearrangements.

So, according to a further embodiment of the method for preparing a compound of formula (I) of the invention, said method is characterized in that a compound of formula (I') is obtained, wherein at least one of the groups selected from $R_1$, $R_{2a}$, $R_{2b}$, $R_3$, $R_4$, $R_5$, $R_7$, $R_{8a}$, $R_{8b}$ and $R_9$ is not a hydrogen atom and is prepared from a compound of formula (I") wherein each of the groups selected from $R_1$, $R_{2a}$, $R_{2b}$, $R_3$, $R_4$, $R_5$, $R_7$, $R_{8a}$, $R_{8b}$ and $R_9$ represents a hydrogen atom, according to a step selected from:

a halogenation reaction, a directed metallation reaction, a Friedel-Craft reaction, a rearrangement reaction, for example a Fries reaction transferring an acyl moiety of an oxygen or a nitrogen to an aromatic one.

Anilines of formula (III) and aromatic derivatives of formula (IV) are commercially available to public and are marketed for example from chemical products suppliers.

Alternatively, compounds of formula (III), like compounds of formula (IV), may be prepared by applying or adapting methods described and familiar to the person skilled in the art.

It may be required in the reactions described hereinbefore to protect some functional groups so as to avoid unwanted by-reactions. These protections may be obtained thanks to techniques described by T. W. Greene and P. G. M. Wuts in Protective Groups in Organic Chemistry, John Wiley and Sons, 1991 or par J. F. W. McOmie in Protective Groups in Organic Chemistry, Plenum Press, 1973.

Compounds of formula (I) may also be prepared through amination of phenothiazines carrying a halogen or a sulfonate at position 2 or 8. Such reaction is preferably effected by coupling with a transition metal such as palladium, nickel or copper.

These transformations of functional groups may be also adapted from the methods described by R. C. Larock in Comprehensive Organic Transformations, VCH publishers, 1989.

Industrial Application for Compounds of Formula (I)

As already previously stated in the present description, compounds of formula (I) possess biocidal properties of industrial interest, after photoactivation.

As opposed to the compounds from the 3,7-diaminophenothiazine family, compounds of formula (I) consist in stable mesomeric bases, which do not suffer from the charge displacement phenomenon that is proper to methylene blue and to the DAP 3-7 series.

Compounds of formula (I) also not have any ionic structure of the phenothiazinium type, that is proper to the 3-7 series.

As already previously specified in the present description, compounds of formula (I) both come as bases and solvates.

It has been generally shown according to the invention that compounds of formula (I) possess at least three activity characteristics which make them different from the known products, including known diaminophenothiazines, i.e. respectively:

compounds of formula (I) consist in white light-photoactivable agents. Thus, to photoactivate compounds of formula (I), it is not necessary to expose these compounds to a light within the ultraviolet radiation wavelength range. When exposed to white light, that is to say to a range of wavelengths of from about 450 nanometers to about 750 nanometers, compounds of formula (I), for example DAP 2-8 tetramethyl (N,N,N',N'-tetramethyl-10H-phenotiazine-2,8-diamine) turn from a yellow shade to a green shade, more exactly to a nickel-green shade.

compounds of formula (I), after photoactivation with white light, have a biocidal activity spectrum, especially against bacteria and parasites, that is very different from the biocidal activity spectrum of methylene blue. In particular, compounds of formula (I) possess a biocidal activity level and spectrum absolutely different from that of methylene blue, the former being active from a concentration of 0.05 per thousand (weight/weight) in distilled water. In addition, compounds of formula (I) are photoactivated by being exposed to a light intensity that is lower than the light intensity required for photoactivating known 3,7-diaminophenothiazine compounds (standardized tests: NF EN 1040).

Some compounds of formula (I), like for example N,N,N', N'-tetramethyl-10H-phenotiazine-2,8-diamine, or N,N-dibutyl-(8-morpholin-4-yl-10H-phenothiazin-2-yl)amine also possess flocculating properties. It has been in particular demonstrated according to the invention that compounds of formula (I) act as protein flocculating agents, either of animal or bacterial origin. It has also been shown that the flocculation effect obtained depends on the amount of the compound of formula (I) added. In practice, the flocculating compound of formula (I) concentrates in the precipitate (floc). The flocculating effect of a compound of formula (I) can be detected from a compound of formula (I) concentration as low as 0.1 per thousand (weight/weight), or even lower (threshold in the vicinity of 0.05 per thousand). A relationship exists between structure and activity of the flocculating capacity, correlated with the length of the side chains and the number of alkane and/or heterocyclic groups (for example piperazine, morpholine). In addition, some compounds of formula (I) spontaneously flocculate under light in distilled water.

It could be taken advantage of the combination all technical effects that may be induced by the compounds of formula (I) in all the industrial applications for which a disinfecting effect is to be obtained.

Very particularly, compounds of formula (I) are useful in the water treatment field, whether it deals with treating water prior to being converted to drinking water, or with wastewater to be treated prior to being released into the natural environment.

Especially DAP-2,8 tetramethyl at concentrations ranging from 100 mg/l to 1000 mg/l does not possess any irritant or corrosive activity in albino rabbits (non-irritant to the skin and eyes according to OCDE 404 and 405 classifications), which is noteworthy to for a biocide agent.

As already described in the section that relates to the description of the prior art, the flocculating/settling step and the disinfecting step are nowadays separate steps in the actual processes for treating fluids, including industrial or domestic effluents. In the usual methods, the flocculating/settling step especially generates sludge very rich in widely diversified microorganism types. That is the reason why in these traditional treatment methods, a subsequent step for disinfecting the fluids is required so as to eliminate these microorganisms, that are sometimes pathogenic for humans and animals, prior to releasing the effluent, once treated, into the environment. As to the resulting sludge, it represents a pool of living organisms of any size and of pollutants, that are potentially dangerous.

So, thanks to the 2,8-diaminophenothiazine compounds of formula (I), it is now possible to simultaneously (i) allow the pollutant settling after flocculation and (ii) perform the disinfection of the fluid being treated.

From now on, by using compounds of formula (I), methods may be developed for treating fluids, especially industrial or domestic effluents, comprising one single step of flocculation/disinfection/settling.

A further advantage of the 2,8-diaminophenothiazine compounds of formula (I) lies in the fact that inducing their biocidal activity does not necessarily require specific photoactivation devices, such as for example ultraviolet radiation-generating devices.

For example, for the 2,8-diaminophenothiazine compounds of formula (I) to exert their flocculating and biocidal combined effects, the flocculation/disinfection step should only be carried out in a pool or a treatment tank exposed to daylight.

So, it is also an object of the present invention to provide the use of a compound of formula (I) such as defined in the present description, as a biocide agent. The use of these compounds as biocide agents may be implemented in the field of fluid disinfection, sterilization or purification.

In some embodiments, said fluids are selected from industrial effluents and domestic effluents.

The invention further relates to a composition for disinfecting, sterilizing or purifying fluids comprising a compound of formula (I) such as defined in the present description.

In some embodiments, said composition is in the form of a support onto which or in which the compound of formula (I) has been immobilized.

So, the products may be incorporated and chemically cross-linked in an inert plastic material, for example of the polyurethane type, with various hardness and forms (plates, beads, powders, foams, blades, fan blades, propellers, etc.). The products are incorporated before polymerization in the form of hydrophobic bases. After reaction, the to plates obtained have various shades. The final concentration of compound(s) of formula (I) ranges from 0.1 to 5% by weight relative to the final composition total weight. These plates can be used as biocidal photoactivation supports under sun-light or artificial light. A controlled water or gas flow under day- or electric light causes molecules and biocidal radicals to be generated, leading to a significant cost-effective and fast reduction of the microbial load in the effluents, which may be stored between two plates. This type of method is particularly adapted to the drinking water closed circuits, as they exist in accommodations without correct water supply lines but having rain water or spring water sources, brooks, reservoirs, etc., of isolated human communities, in boats, planes, trains, mobile units in hostile environments, etc. The reaction being of the catalytic type, there is no product salting-out upon disinfection.

The method may also be implemented for treating gases and distribution networks (air conditioning systems, aerorefrigerant towers, medical gases or industrial gases). The gas may be supplied to suitable white light-illuminated systems. DAP 2-8 may then be incorporated into an inert support of the plastic or the ceramic type, or into a porous inert support, for example nonwowen materials, cellulose derivatives or any other open-cell structures.

Immobilizing the product onto the support may be done in a covalent or a non covalent manner. With a covalent bond, the product to immobilize should have a reactive site allowing the bonding to the support upon the polymerization reaction. For example, the product may comprise an alcohol in one of the $R_1$, $R_3$, $R_4$, $R_6$, $R_7$, $R_9$, $R_{2a}$, $R_{2b}$, $R_{8a}$ or $R_{8b}$ substituents, which will react with an isocyanate during the preparation of a polyurethane support. With a non covalent bond, the product may be combined with at least one of the monomers before the polymerization reaction. II is also possible to apply the product onto the support, optionally by diluting it in a solvent such as water or in an organic solvent. Application may be effected by dipping the support, spraying the diluted product or by means of a brush or a roller.

The present invention will be now illustrated through the embodiments thereof described hereunder in the following examples.

EXAMPLES

Example 1

N,N,N',N'-tetramethyl-10H-phenothiazine-2,8-diamine

Step A: bis-(3-dimethylaminophenyl)amine

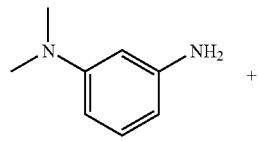

+

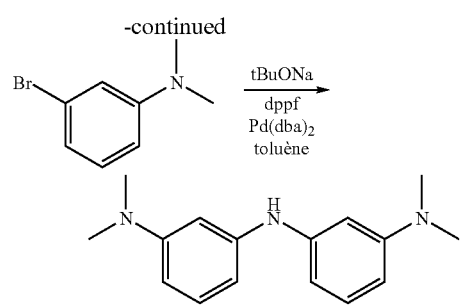

Under dinitrogen atmosphere, 1 equivalent of 3-bromo-N,N-dimethylaniline (1 g), 1.5 equivalent of sodium tert-butylate (0.721 g), 0.1 equivalent of Pd(dba)$_2$ (0.288 g), 0.12 equivalent of dppf (0.555 g) and 20 mL of toluene are introduced into a flask. The flask is fitted with a PTFE septum and 1.2 equivalent of N,N-dimethylbenzene-1,3-diamine (0,817 g) is added thereto using a syringe. The reaction medium is heated at 90° C. for 12 hours, thereafter is cooled to room temperature and concentrated under reduced pressure. The product is purified by flash chromatography using a gradient of 5% to 12% of ethyl acetate in hexane (Rf: 0.33) to give 0.963 g of the expected product with a yield of 75%.

NMR $^1$H: (CDCl$_3$) 7.13 (t, 2H), 6.5 (d, 2H), 6.49 (d, 2H), 6.38-6.36 (m, 2H), 5.68 (s large, 1H), 2.95 (s, 12H).

MS (M+1): 256

Step B: N,N,N',N'-tetramethyl-10H-phenothiazine-2,8-diamine

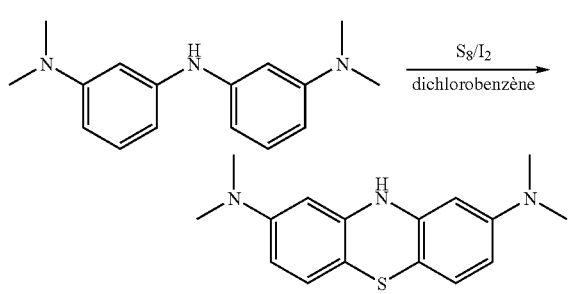

A mixture of bis-(3-dimethylaminophenyl)amine (0.5 g, 1.9 mmol), of sulfur (0.15 g, 4.6 mmol) and iodine crystal in 4 mL of o-dichlorobenzene is heated under reflux under dinitrogen atmosphere for 3 h. Once back to room temperature, the mixture is extracted with diethyl ether (15 mL), filtered and concentrated under reduced pressure.

The corresponding oil is chromatographed on a silica gel with toluene as an eluent to give a brown powder (140 mg).

Coupling General Procedure:

Under inert atmosphere (argon), to the brominated aromatic compound IV (1 equiv) solutioned in toluene (4 mL per mmol) are successively added aniline III (1.2 equiv) then Pd(dba)2 (0.05 equiv), dppf (0.1 equiv) and tBuONa (1.5 equiv). The reaction mixture is degassed and placed under argon atmosphere, then brought to toluene reflux temperature for 8 to 14 hours (until IV has completely disappeared). The reaction mixture is then brought back to room temperature, partitioned between water and ethyl acetate and then extracted with ethyl acetate (twice). The organic phases are collected, dried over sodium sulfate and the solvents are evaporated. The raw mixture is purified by chromatography on a silica gel to provide diarylamine II with yields over 60%.

Eluents: cyclohexane-ethyl acetate 80:20 to 60:40 except for compounds comprising N-methyl piperazine for which dichloromethane and methanol are used (90:10 to 80:20).

Phenothiazines I Preparation General Procedure:

To a solution of diarylamine II (1 equiv) in 1,2-dichlorobenzene (1 mL for 100 mg of substrate) held under argon atmosphere are added sulfur (0.3 equiv) and iodine crystal. The reaction mixture is brought to reflux and maintained under stirring at this temperature for 4 to 5 hours. Once back to room temperature, to the reaction mixture is added dichloromethane and a sodium thiosulfate saturated solution. After settling, the organic phase is separated from the aqueous phase and then dried over sodium sulfate. After dichloromethane is evaporated, the raw reaction mixture solutioned in 1,2-dichlorobenzene is directly purified by chromatography on a silica gel to provide phenothiazine I with yields which vary depending on the substrates used [the chromatography column is protected against light by means of an aluminium sheet]. Under some circumstances, the substrate after purification is solubilized in hot diethyl ether to which black carbon is added. The mixture is filtered through a Celite bed and solvent is evaporated to give, in general, phenothiazine I as a light brown solid.

Eluents: cyclohexane-ethyl acetate 80:20 to 60:40 except for compounds comprising N-methylpiperazine for which dichloromethane and methanol are used (90:10 to 80:20).

Phenothiazine I Chlorhydrate Preparation General Procedure:

To phenothiazine as a base solutioned in abs. ethanol (3 to 12 mL for 0.3 mmol, depending on the substrates) is added at a temperature near 0° C. a solution of HCl in diethyl ether (2 N, 4 equiv, 1.2 mmol). The reaction mixture is stirred for 15 minutes at a temperature near 0° C., and then solvents are evaporated under reduced pressure. The residue is triturated with anhydrous diethyl ether until a solid is obtained. This solid is separated on a sintered filter, washed many times with anhydrous diethyl ether and then dried in an oven under vacuum. Phenothiazine chlorhydrates are isolated with yields around 90%.

By following these general procedures, the following products were prepared, which are characterized by their magnetic nuclear resonance spectrum at 270 MHz performed on chlorhydrate solutioned in deuterated methanol:

| Example | Structure | NMR |
|---|---|---|
| 2 | 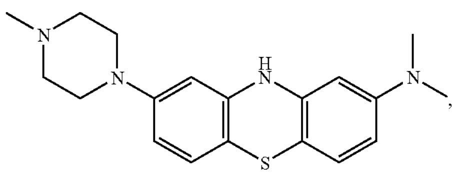 | 2.90 (3 H, s), 3.30 (10 H, large m), 3.55 (2 H, m), 3.80 (2 H, br s), 7.05 (6 H, m) |
| 3 | 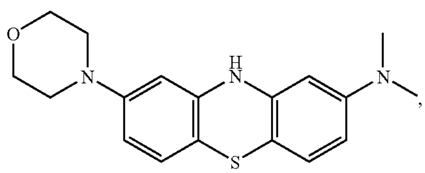 | 3.23 (6 H, m), 3.61 (4 H, m), 4.09 (4 H, m), 7.03 (6 H, m) |
| 4 | 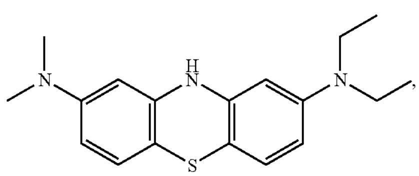 | 1.15 (6 H, m), 3.15 (6 H, br s), 3.45 (4 H, br s), 7.05 (6 H, m) |
| 5 | 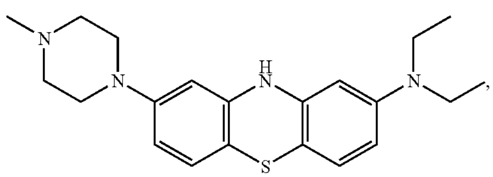 | 1.17 (6 H, t, J = 7.0 Hz), 2.95 (3 H, s), 3.05-3.90 (12 H, br m), 6.45 (2 H, br s), 7.05 (4 H, br m) |
| 6 | 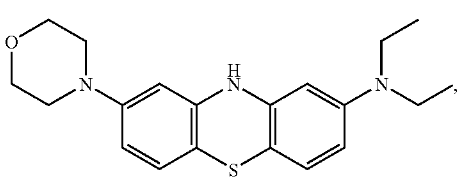 | 1.17 (6 H, t, J = 7.0 Hz), 3.48 (8 H, m), 4.05 (4 H, m), 7.05 (6 H, m) |
| 7 | 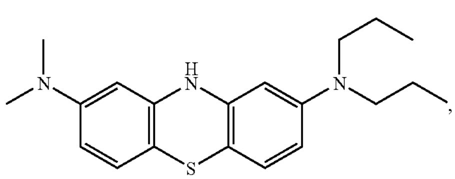 | 0.95 (6 H, br t, J = 7.3 Hz), 1.49 (4 H, m), 3.29 (6 H, br s), 3.50 (4 H, m), 7.05 (6 H, m) |

-continued

| Example | Structure | NMR |
|---|---|---|
| 8 | [3,7-bis(amino)phenothiazine with N-methylpiperazine and N,N-dipropylamine substituents], 3HCl | 0.95 (6 H, m), 1.52 (4 H, m), 2.90-3.80 (15 H, m), 6.50-7.05 (6 H, m) |
| 9 | [3,7-bis(amino)phenothiazine with morpholine and N,N-dipropylamine substituents], 2HCl | 0.95 (6 H, br t, J = 6.8 Hz), 1.55 (4 H, m), 3.50 (4 H, m), 3.60 (4 H, m), 4.08 (4 H, m), 7.00 (6 H, m) |
| 10 | [3,7-bis(amino)phenothiazine with N,N-dimethylamine and N,N-dibutylamine substituents], 2HCl | 0.91 (6 H, m), 1.15-1.55 (8 H, m), 3.39 (6 H, br s), 3.55 (4 H, m), 7.05 (6 H, m) |
| 11 | [3,7-bis(amino)phenothiazine with N-methylpiperazine and N,N-dibutylamine substituents], 3HCl | 0.95 (6 H, m), 1.35 (6 H, m), 1.59 (2 H, m), 2.90-3.90 (15 H, m), 6.50-7.05 (6 H, m) |
| 12 | [3,7-bis(amino)phenothiazine with morpholine and N,N-dibutylamine substituents], 2HCl | 0.90 (6 H, m), 1.35 (8 H, m), 3.01 (4 H, m), 3.50 (4 H, m), 3.82 (4 H, m), 4.06 (2 H, m), 6.91 (6 H, m), |
| 13 | [3,7-bis(amino)phenothiazine with N,N-dimethylamine and N-ethylamine substituents], 2HCl | 1.04 (3 H, br t, J = 7.4 Hz), 1.75 (2 H, m), 3.23-3.32 (8 H, m), 6.90 (6 H, m) |
| 14 | [3,7-bis(amino)phenothiazine with N,N-dimethylamine and N-methylamine, 3-methyl substituents], 2HCl | 2.35 (s, 3 H), 3.25-3.29 (m, 6 H), 6.93-7.06 (m, 5 H) |

Moreover, some products have also been characterized by a carbon-13 NMR of chlorhydrate at 62.5 MHz in deuterated methanol:

| Example | Structure | NMR |
|---|---|---|
| 13 | [3,7-bis(amino)phenothiazine with N,N-dimethylamine and N-ethylamine substituents], 2HCl | 8.87, 18.23, 44.77, 52.51, 105.20, 107.35, 112.51, 115.20, 118.10, 118.66, 126.49, 126.65, 134.10, 141.52, 141.94, 142.09 |

| Example | Structure | NMR |
|---|---|---|
| 14 | (phenothiazine structure with dimethylamino groups), 2HCl | 16.35, 46.98, 47.19, 106.57, 120.59, 121.10, 124.50, 124.96, 128.86, 130.69, 141.46, 142.27, 144.05, 144.26 |

The structure of some examples has also been confirmed by high resolution mass spectrometry experiments.

| Example | analysis |
|---|---|
| 10 | calcd: 369.2238; found: 369.2272 |
| 11 | calcd: 424.2661; found: 424.2694 |
| 13 | calcd: 299.1456; found: 299.1468 |

The melting point is given for some bases as an indication.

| Example | melting point |
|---|---|
| 8 | 122-124° C. |
| 11 | 150-152° C. |
| 13 | 158-160° C. |

Example 15

2-[N-(8-dimethylamino-10H-phenothiazin-2-yl)-N-(2-hydroxyethyl)amino]ethanol and 2-[N-(8-dimethylamino-10H-phenothiazin-2-yl)-N-(2-hydroxyethyl)amino]ethanol dichlorhydrate Step 15.1: (3-bromophenyl)-bis-[2-(tert-butyldimethylsilanyloxy)ethyl]amine Under argon atmosphere, a mixture of 2-[N-(3-bromophenyl)-N-(2-hydroxyethyl)amino]ethanol (1.15 g, 4.42 mmol), of tert-butyldimethylsilyl chloride (3 equiv, 2.0 g, 13.27 mmol) and of imidazole (6 equiv, 1.8 g, 26.5 mmol) in dichloromethane (40 mL) is stirred at room temperature overnight. After partition of the reaction mixture between dichloromethane and water, extractions are performed with dichloromethane (twice). The organic phases are collected, dried over sodium sulfate, filtered and the solvent is removed. After purification by chromatography on a silica gel, (3-bromophenyl)-bis-[2-(tert-butyldimethylsilanyloxy)ethyl]amine is obtained as a colorless oil.

1H NMR (270 MHz, CDCl3): δ (ppm): 0.03 (12H, m), 0.88 (18H, m), 3.47 (4H, t, J=6.2 Hz), 3.74 (4H, t, J=6.2 Hz), 6.61 (1H, br d, J=8.1 Hz), 6.75 (1H, br d, J=8.1 Hz), 7.6 Hz), 6.84 (1H, br s), 7.01 (1H, br t, J=8.1 Hz)

Step 15.2: [3-(3-dimethylaminophenylamino)phenyl]-bis-[2-(tert-butyldimethylsilanyloxy)ethyl]amine By proceeding as described in the coupling general procedure, but starting from 1.85 g (3.8 mmol) of (3-bromo-phenyl)-bis-[2-(tert-butyldimethylsilanyloxy)ethyl]amine and 1.15 g (4.42 mmol) of N,N-dimethylbenzene-1,3-diamine, [3-(3-dimethylaminophenylamino)phenyl]-bis-[2-(tert-butyldimethylsilanyloxy)ethyl]amine is obtained as a pale yellow oil.

$^1$H NMR (270 MHz, CDCl$_3$): δ (ppm): 0.02 (12H, m), 0.88 (18H, br s), 2.92 (6H, br s), 3.47 (4H, t, J=6.2 Hz), 3.74 (4H, t, J=6.2 Hz), 5.61 (1H, br s), 6.28 (2H, m), 6.40 (4H, m), 7.10 (2H, m)

Step 15.3: N,N-bis-(tert-butyldimethylsilanoxy)ethyl-N',N'-dimethyl-10H-phenothiazine-2,8-diamine By proceeding as described in phenothiazine preparation general procedure, but starting from 1.85 g (3.4 mmol) of [3-(3-dimethylaminophenylamino)phenyl]-bis-[2-(tert-butyldimethylsilanyloxy)ethyl]amine and 260 mg (0.1 mmol) of sulfur, N,N-bis-(tert-butyldimethylsilanoxy)ethyl-N',N'-dimethyl-10H-phenothiazine-2,8-diamine is obtained, isolated as a brown solid.

Step 15.4: 2-[N-(8-dimethylamino-10H-phenothiazin-2-yl)-N-(2-hydroxyethyl)amino]ethanol To a solution of N, N-bis-(tert-butyldimethylsilanoxy)ethyl-N',N'-dimethyl-10H-phenothiazine-2,8-diamine (1.08 g, 1.88 mmol) in tetrahydrofuran (20 mL) is added a solution of tetrabutylammonium fluoride 1M in tetrahydrofuran (2.5 equiv, 4.7 mL, 4.7 mmol). The mixture is stirred for one hour at room temperature (until complete removal of starting material after CCM). The thus formed suspension is filtered off. The precipitate is washed with tetrahydrofuran, and then solubilized in a mixture of water and ethyl acetate. The organic phase is then washed many times with water, dried over sodium sulfate. After solvent removal, a light, dark brown solid is obtained.

Step 15.5: 2-[N-(8-dimethylamino-10H-phenothiazin-2-yl)-N-(2-hydroxyethyl)amino]ethanol dichlorhydrate By proceeding as described in chlorhydrate preparation general procedure, but starting from 2-[N-(8-dimethylamino-10H-phenothiazin-2-yl)-N-(2-hydroxyethyl)amino]ethanol, 2-[N-(8-dimethylamino-10H-phenothiazin-2-yl)-N-(2-hydroxyethyl)amino]ethanol dichlorhydrate is obtained.

1H NMR (270 MHz, CDCl3): δ (ppm): 3.9 (6H, m), 3.60 (8H, m), 7.05 (6H, m).

Photoactivation Properties of Compounds of Formula (I)

The biocidal tests were carried out according to Directive NF EN 1040. Tests were conducted at the same time in the dark and under white light, corresponding to a moderate sunshine (400 KJ/M2) using an ordinary incandescent or halogen lamp. Some tests may be carried out up to 1.3 mW/Cm$^2$ Phenothiazine-2,8-diamines (DAP-2,8) of the invention, in the form of dichlorhydrates, are solutioned (100 mg/l) in bi-distilled water or PPI type water. For example, the color of the N,N,N',N'-tetramethyl-10H-phenotiazine-2,8-diamine solution turns from yellow to nickel-green in less than 15 minutes. The color change is all the more fast that the solution is illuminated under white light. The tests are performed in sterile glass flasks according to disinfection test standards. Illumination is a sun light illumination or an artificial light illumination and is compared with tests carried out in the dark (glass material is wrapped with aluminium foil).

Biocidal Properties of Compounds of Formula (I)

1) As Powders

Biocidal activity tests are carried out according to EN standards, for example EN 1040, EN 1275, on reference microbial strains registered under ATCC and CIP, and validated by an accredited laboratory. Example of N,N,N',N'-tetramethyl-10H-phenothiazine-2,8-diamine action spectrum.

| Strain | Concentration (distilled water) | Contact time | Infectious titer reduction (log) |
|---|---|---|---|
| *Legionella pneumophila* subsp *pneumophila* CIP 103 854 | 100 mg/l | 15 to 30 mn | >5.5 |
| *Pseudomonas aeruginosa* CIP 103 467 | 50 to 100 mg/l | 15 to 30 mn | >5.5 |
| *Escherichia coli* CIP 54 127 | 50 to 100 mg/l | 15 to 30 mn | >5.5 |
| *Candida albicans* IP 48.72 | 100 mg/l | 30 mn | 3.2 |

These tests validate as biocide agents as defined by the European pharmacopoeia if the infectious titer reduction is higher than 5.

Tests are carried out under white light versus a control in the dark. In all cases, white light accelerates the biocidal phenomenon, for example the biocidal activity under light requires a 15 min-contact time, as opposed to 30 mn in the dark.

It should be noted that the DAP 2,8 series may have a "range effect", that is to say there is a concentration range that is more efficient as compared to higher concentrations. For example, N,N,N',N'-tetramethyl-10H-phenothiazine-2,8-diamine is more efficient under light with 30 mn of contact on *Candida albicans* IP 48.72 at 100 mg/l (infectious titer reduction 3.2 log) than at 250 or 500 mg/l (infectious titer reduction <2.8 log).

Flocculation Properties of Compounds of Formula (I)

In the presence of proteins or yeast extracts, the DAP-2,8 series precipitate spontaneously the culture media (bovine albumin, yeast extract), by forming a brown-colored floc. The higher the protein concentration in the solution, the strongest the flocculation. DAP-2,8 do concentrate in this floc. For example in a 10 g/l yeast extract solution, more than 70% of the initial amount of DAP is recovered in the pellet. The flocculating activity is all the more important:

that side chains located at 2-8 comprise heterocycles, for example a morpholine or piperazine moiety.

And/or that side chains comprise alkyl moieties of increasing MW (butyl derivatives are more efficient than propyl derivatives, which in turn are more efficient than ethyl and last methyl moieties).

The flocculating activity of the DAP 2-8 series appears, depending on structures, from 0.05 per thousand. In addition, the flocculating activity appears by diffusing in agar medium, when DAP 2-8-impregnated discs are deposited onto a bacterial culture in a solid medium (for example, Müller Hinton medium). Flocculation rings around the impregnated discs can be observed.

2) Biocidal Support

Products in the form of bases are incorporated into inert plastic materials of the polyurethane type, or any other inert hydrophobic support. Products can then be used for disinfection/purification/deodorization purposes for liquid or gaseous fluids. Illuminating the plates induces the production in situ of singlet oxygen and biocidal radicals from the ambient or dissolved oxygen. The reaction is of the catalytic type. The form these plastic materials may take varies depending on their intended use: assembled blades, sloping plates, powders, beads, fan blades, propellers, etc. It is then possible to incorporate DAP 2-8, for example in the form of solvates, into hydrophilic porous supports.

Preparation example: 0.018 g of DAP-2,8 tetramethyl coming as a base are suspended in 11.075 g of polyol. After stirring at room temperature, the whole polyol turns to a clear yellow shade. Adding thereto 0.016 g, then 0.086 g of DAP-2,8 tetramethyl, followed with a stoving at 70° C. causes its complete dissolution. The final concentration is of 0.120 g of DAP-2,8 tetramethyl in 11.075 g of polyols.

Polymerizing with isocyanate in an amount of 6/10 (w/w) enables to produce a polyurethane solid of the PRC 1700 type. Plates are made in two successive casts, the first one with polyols+DAP-2,8 tetramethyl in a thin layer; the second one without DAP is cold cast after complete polymerization of the first cast.

A polyurethane plate comprising N,N,N',N'-Tetramethyl-10H-phenothiazine-2,8-diamine (not covalent) or 2-[(8-Dimethylamino-10H-phenothiazin-2-yl)-(2-hydroxy-ethyl)-amino]-ethanol (covalent bond) reduces in 1 hour under a white light more than 1 log of the *Escherichia coli* CIP 54 127 infectious titer. The control in the dark under the same conditions has no activity at all.

The invention claimed is:

1. A 2,8-diaminophenothiazine compound of formula (I):

$$
\begin{array}{c}
R_{8a} \quad R_9 \quad\quad\quad H \quad\quad\quad R_1 \quad R_{2a} \\
R_{8b}-N \quad\quad\quad N \quad\quad\quad N-R_{2b}, \\
R_7 \quad\quad\quad\quad\quad S \quad\quad\quad\quad R_3 \\
R_6 \quad\quad\quad\quad R_4
\end{array}
$$
(I)

wherein:

(i) $R_1$, $R_3$, $R_4$, $R_6$, $R_7$ and $R_9$ groups each represent, independently from one another, a group selected from the group consisting of:
a hydrogen atom,
a halogen,
an alkyl group having from 1 to 12 unsubstituted carbon atoms, and
an alkyl group having from 1 to 12 carbon atoms substituted by a phenyl group, said phenyl group being:
either unsubstituted,
or substituted by one or more groups selected from a halogen, a hydroxy, an alkyl having from 1 to 12 carbon atoms, and an alkoxy having from 1 to 12 carbon atoms, and (ii) $R_{2a}$, $R_{2b}$, $R_{8a}$ and $R_{8b}$ groups each represent, independently from one another, a group selected from the group consisting of:
an alkyl group, a hydroxyalkyl group or an alkoxyalkyl group having from 1 to 12 unsubstituted carbon atoms, and
an alkyl group or an alkoxyalkyl group having from 1 to 12 carbon atoms substituted by a phenyl group, said phenyl group being:
either unsubstituted,
or substituted by a group selected from the group consisting of:
a halogen,
a hydroxy,
an alkyl having from 1 to 12 carbon atoms,
an alkoxy having from 1 to 12 carbon atoms,
an akenyl having from 2 to 12 carbon atoms, unsubstituted or substituted by a group selected from a halogen, a hydroxy, an alkyl having from 1 to 12 carbon atoms, an alkoxy having from 1 to 12 carbon atoms,
an alkynyl having from 2 to 12 carbon atoms, unsubstituted or substituted by a group selected from a halogen, a hydroxy, an alkyl having from 1 to 12 carbon atoms, an alkoxy having from to 12 carbon atoms,
a cycloalkyl having from 4 to 12 carbon atoms, unsubstituted or substituted by a group selected from a halogen, a hydroxy, an alkyl having from 1 to 12 carbon atoms, an alkoxy having from 1 to 12 carbon atoms, and
a cycloalkenyl having from 4 to 12 carbon atoms, unsubstituted or substituted by a group selected from a halogen, a hydroxy, an alkyl having from 1 to 12 carbon atoms, an alkoxy having from 1 to 12 carbon atoms, (iii) or $-NR_{2a}R_{2b}$ or $-NR_{8a}R_{8b}$ groups, independent from one another, represent a heterocycle having from 4 to 12 carbon atoms, either saturated or unsaturated, where said heterocycle may comprise one or more additional heteroatoms selected from nitrogen, oxygen and sulfur, said heterocycle being unsubstituted or being substituted by a group selected from a halogen, a hydroxy and an alkyl having from 1 to 12 carbon atoms,
or a salt, hydrate, solvate, or polymorphic form thereof.

2. The compound of claim 1, wherein at least one and at most four of the groups selected from $R_{2a}$, $R_{2b}$, $R_{8a}$ and $R_{8b}$ represent(s) a methyl group.

3. The compound of claim 1, selected from the group consisting of:
N,N,N',N'-Tetramethyl-10H-phenothiazine-2,8-diamine;
N,N-Diethyl-N',N'-dimethyl-10H-phenothiazine-2,8-diamine;
N,N-Dimethyl-N',N'-dipropyl-10H-phenothiazine-2,8-diamine; and
N,N-Dibutyl-N',N'-dimethyl-10H-phenothiazine-2,8-diamine.

4. A composition comprising the compound of claim 1 as a biocide agent.

5. A composition comprising the compound of claim 1, wherein the compound has been photoactivated and has biocidal activity.

* * * * *